United States Patent [19]

Knifton

[11] Patent Number: 4,554,383

[45] Date of Patent: Nov. 19, 1985

[54] PROCESS FOR PRODUCING P-TOLUALDEHYDE FROM TOLUENE USING AN ALUMINUM HALIDE ALKYL PYRIDINIUM HALIDE 'MELT' CATALYST

[75] Inventor: John F. Knifton, Austin, Tex.

[73] Assignee: Texaco Inc., White Plains, N.Y.

[21] Appl. No.: 644,118

[22] Filed: Sep. 20, 1984

[51] Int. Cl.$^4$ ............................................. C07C 45/49
[52] U.S. Cl. .................................................. 568/428
[58] Field of Search ............................... 568/428, 429

[56] References Cited

U.S. PATENT DOCUMENTS

| | | | |
|---|---|---|---|
| 2,485,237 | 10/1949 | Greshman et al. | 568/428 |
| 3,948,998 | 4/1976 | Fujiyama et al. | 568/428 |
| 4,195,040 | 3/1980 | Renner | 568/428 |
| 4,218,403 | 8/1980 | Vanderpool | 568/428 |

FOREIGN PATENT DOCUMENTS 0064690  11/1982  European Pat. Off. ............ 568/428

OTHER PUBLICATIONS

Kulka, "Amer. Perfume Aromatics" vol. 69 (Feb. 1969), pp. 31–33.
Gray et al., "J. Amer. Chem. Soc." vol. 103 (1982), pp. 7147–+.

*Primary Examiner*—Werren B. Lone
*Attorney, Agent, or Firm*—Jack H. Park; Kenneth R. Priem; Cynthia L. Kendrick

[57] ABSTRACT

A process for the selective carbonylation of toluene to p-tolualdehyde which comprises mixing an N-alkylpyridinium halide and an anhydrous aluminum halide melt catalyst with toluene, at room temperature of higher and at superatmospheric pressure until the desired tolualdehyde is formed, and separating the desired product.

6 Claims, No Drawings

PROCESS FOR PRODUCING P-TOLUALDEHYDE FROM TOLUENE USING AN ALUMINUM HALIDE ALKYL PYRIDINIUM HALIDE 'MELT' CATALYST

FIELD OF THE INVENTION

This invention relates to the production of an aromatic aldehyde such as p-tolualdehyde, and more particularly to the novel use of an aluminum halide-alkyl pyridinium 'melt' catalyst for the selective carbonylation of toluene to p-tolualdehyde. p-Tolualdehyde, a precursor for terephthalates, is generated with high selectivity.

BACKGROUND OF THE INVENTION

Various processes have been proposed to produce aromatic aldehydes such as p-tolualdehyde. Generally these methods involve reacting an alkyl-substituted aromatic hydrocarbon, such as toluene with carbon monoxide in the presence of some type of catalyst system.

G.B. Pat. No. 1,422,308 to Mitsubishi discloses a process for continuous production of aromatic aldehydes which comprises passing a reaction liquid comprising an aromatic hydrocarbon, hydrogen fluoride and boron trifluoride through a tubular reaction zone.

U.S. Pat. No. 2,485,237 discloses a process for the low temperature synthesis of aromatic aldehydes which also uses hydrogen fluoride and boron trifluoride, and which claims that this invention results in high yields of desired aldehyde products and, further, allows for easier separation of said product from catalyst.

In U.S. Pat. No. 3,948,998 another two-step process is disclosed for producing p-tolualdehyde which involves a catalyst system similar to that of the previously discussed references, but is characterized by reacting a preformed toluene-hydrogen floride-boron trifloride complex with carbon monoxide, thereby converting a portion of the toluene to p-tolualdehyde, and then adding the remainder of the $BF_3$ to the reaction product and reacting the remainder of the toluene with carbon monoxide.

U.S. Pat. No. 4,218,403 discloses a catalyst system for producing aromatic aldehydes by reacting an alkylbenzene with carbon monoxide in the presence of a tantalum, niobium or antimony pentafluoride-hydrogen flouride catalyst system.

Gale, Gilbert and Osteryoung discuss the use of aluminum halide-alkylpyridinium halide mixtures as aprotic molten salt media in Inorg. Chem. 17, 2728 (1978).

In *Inorganic Chemistry*, Vol. 18, p. 1603, 1979, Gale and Osteryoung disclose the results of potentiometric work on the solvent acid-base properties of $AlCl_3$:N-butyl pyridinium chloride and an equilibrium constant for the dissociation reaction of $AlCl_4^-$ was determined.

Gray and Maciel completed an Al NMR spectra study on liquid samples consisting of mixtures of $AlCl_3$ and N-butylpyridinium chloride at various mole ratios and at various temperatures and have determined parameters for the $AlCl_4^-$ and $Al_2Cl_7^-$ ions in these melts and have estimated a chemical exchange rate. See J. Am. Chem. Soc., Vol. 103, p. 7147, 1981.

In the reaction of aromatic hydrocarbons with carbon monoxide in the presence of aluminum chloride and hydrogen chloride, stoichiometric amounts of the catalyst have generally been used. High yields of benzaldehyde and tolualdehyde can be obtained, but the scope of the reaction is limited since higher alkylbenzenes generally undergo scrambling via alkylation-dialkylation steps. Although carbonylation of aromatics also proceeds smoothly in the presence of $HF/BF_3$, an obstacle to commercialization has been the difficulty of recycling the catalyst. See *Chemicals from Syngas* by R. A. Sheldon, D. Reidel Co., 1983, P. 122.

These methods suffer from one or more process deficiencies. For example, most of these processes resort to subambient temperatures, which of course involve some considerable process control. In other cases, large excesses of catalyst must necessarily be employed to carry out the synthesis to obtain appreciable yields. In still other instances, useful catalysts are highly corrosive leading to obvious problems. Lastly, in some the reaction is effected only at high pressures.

SUMMARY OF THE INVENTION

The present invention provides a method for preparing p-tolualdehyde by reacting under superatmospheric pressure carbon monoxide and a toluene in the presence of a novel 'melt' catalyst system. The catalyst comprises aluminum chloride and N-butylpyridinium chloride. An improvement over prior work is that the process can be carried out at ambient temperatures. In addition, an excess of catalyst is not necessary as used often in prior work; the system performs well using only one equivalent of catalyst.

DETAILED DESCRIPTION OF THE INVENTION

According to the present invention p-tolualdehyde is produced in good yields by a process comprising mixing an N-alkylpyridinium halide and an anhydrous aluminum halide 'melt' catalyst with toluene at superatmospheric pressures until the desired tolualdehyde is formed and separating the desired product. Improvements comprise use of ambient temperatures along with lack of necessity of using excess catalyst.

The alkyl-substituted aromatic hydrocarbon, which is toluene, is introduced along with the melt catalyst into a pressure reactor. Thereafter carbon monoxide is introduced under pressure. The aluminum halide-alkylpyridinium halide catalyst is mixed with the toluene. A solvent can be employed, but is not required.

Catalysts that are suitable in the practice of the invention contain aluminum and a halide. The aluminum halide may be chosen from a variety of compounds. It is only necessary that the catalyst employed be water-free (anhydrous) and contain aluminum in its halide form. The catalytically active species is believed to comprise aluminum halide and an N-alkylpyridinium salt in complex combination with carbon monoxide and toluene. The most effective embodiment is achieved where the aluminum species is solubilized in the N-alkylpyridinium salt under reaction conditions.

The aluminum halide may take several different forms. For example, the aluminum halide may be added to the reaction mixture as anhydrous aluminum chloride, anhydrous aluminum bromide, and anhydrous aluminum fluoride. The preferred aluminum halide is anhydrous aluminum chloride, $AlCl_3$.

The aluminum halide is, prior to its catalytic use in making tolualdehyde, first dispersed in a low melting alkyl pyridinium halide. It is interesting to note that the aluminum compound alone, without being dispersed in said salt produces comparatively very low yields of tolualdehyde.

Suitable N-alkylpyridinium salts have the formula:

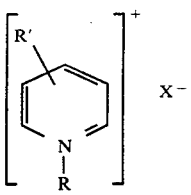

wherein X is a halogen, the R function may be selected from the groups including the alkyl, aryl, and alkaryl radicals containing one to twenty carbon atoms, and R' may be an alkyl or aryl radical containing one to twelve carbon atoms. Alternatively, suitable quaternary N-heterocyclic salts may include certain N-alkylquinolinium halides or other polynuclear N-heterocylic salts.

Examples of suitable quaternary salt compounds useful in this process include N-methylpyridinium chloride, N-butylpyridinium chloride, N-propylpyridinium chloride, N-ethylquinolinium iodide, N-ethylpyridinum bromide and methyl α-picolinium iodide. The preferred N-heterocyclic salt is N-butylpyridinium chloride.

In prior work the conversion of toluene to p-tolualdehyde depended in great measure upon the amount of catalyst used. Generally, the larger the amount of catalyst used the higher the conversion of toluene to p-tolualdehyde. In this invention, the ratio of toluene to catalyst mixture may range from 0.1 to 10; the preferred embodiment contemplates the use of one equivalent of catalyst for each mole of toluene.

The quantity of catalyst employed in the instant invention is not critical and may vary over a wide range. In general, the improved process is desirably conducted in the presence of a catalytically effective quantity of the active aluminum species, and N-heterocyclic quaternary salt which gives the desired products in reasonable yields. The reaction proceeds when employing as little as about $1 \times 10^{-6}$ weight percent, and even lesser amounts, of aluminum halide together with about $1 \times 10^{-6}$ weight percent of N-alkylpyridinium salt, basis the total weight of the reaction mixture. The upper concentration is dictated by a variety of factors including catalyst cost, partial pressures of carbon monoxide and hydrogen, operating temperature etc. A catalyst concentration of from about 0.1 to about 40 weight percent aluminum halide in conjunction with a low melting alkyl pyridinium salt concentration of from about 0.1 to about 40 weight percent based on the total weight of reaction mixture is generally desirable in the practice of this invention. The preferred aluminum halide to N-heterocyclic quaternary salt molar ratio is from about 0.1 to about 10.

Related processes found in the art use and require subambient temperatures. However it is now possible to use ambient temperatures to carry out the process of this invention. The reaction may be run at ambient temperatures and usually can be effected over a range from about 0° C. to 200° C. Most preferably the temperature of the reaction is 100° C.

The reaction itself involving gaseous carbon monoxide is usually run under superatmospheric pressures, ranging from about 1 atm to about 300 atm. More often the pressure is about 200 atm.

The time of the reaction may vary, but the usual reaction time is from 1–6 hour with 4 hours preferable.

Particularly in continuous operations, but also in batch experiments, the carbon monoxide gaseous charge may also be used in conjunction with up to 50% by volume of one or more other gases. These other gases may include one or more inert gases such as nitrogen, argon, neon and the like, or they may include gases that may or may not undergo reaction under CO carbonylation conditions, such as hydrogen, carbon dioxide, hydrocarbons such as methane, ethane, propane and the like, ethers such as dimethyl ether, methylethyl ether and diethyl ether, alkanols such as methanol and acid esters such as methyl acetate.

In all these syntheses, the amount of carbon monoxide present in the reaction mixture should be sufficient to at least satisfy the stoichiometry of the desired oxonation reaction.

The major by-products of this p-tolualdehyde synthesis is most commonly o-tolualdehyde, which is, of course, also a useful compound. The tolualdehydes can be separated from one another by conventional means, e.g. fractional distillation in vacuo.

The aldehyde products may be readily separated from the aluminum catalyst-containing crude product mixture by conventional means, e.g., by fractional distillation in vacuo. The by-products identified supra may also be isolated by conventional means, or they may be recycled with the aluminum halide-quaternary N-heterocyclic salt catalyst.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired alcohol product, and said material may be recovered by methods well known in the art, such as distillation, fractionation, extraction and the like. A fraction rich in aluminum halide-quaternary N-heterocyclic salt catalyst components may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures are in atmospheres (atm).

Having described the inventive process, the following examples are submitted to supply specific and illustrative embodiments:

The invention is further illustrated by the following examples. It is understood, of course, that these examples are merely illustrative and that the invention is not to be limited thereby.

EXAMPLE I

A mixture of N-butylpyridinium chloride (8.58 g, 50 mmole), aluminum chloride (anhydrous, 6.67 g, 50 mmole) and toluene (10.0 g, 109 mmole) was transferred in a glass liner under argon purge to an 850 ml capacity pressure reactor, equipped with heating and means of agitation. The reactor was sealed, flushed with CO and pressured to 204 atm. with carbon monoxide, and the mixture heated to 100° C., with agitation, for four hours.

On cooling, the excess gas was sampled and vented, and the cloudy, pale-yellow liquid recovered. Total liquid recovered was 25.8 g, some solids reappear upon standing.

Analysis of the liquid product by glc showed the presence of:
p-tolualdehyde: 6.6%
o-tolualdehyde: 0.9%
unreacted toluene: 90.7%
unidentified material: 1.8%

Product tolualdehydes were confirmed by nmr and glc - FTIR.

Calculated p-tolualdehyde selectivity = 71%

EXAMPLES II–VII

The same operating conditions were used in Examples II14 VII as were used in Example I. Examples VI and VII are comparative and demonstrate the results when either component of the aluminum chloride-N-alkylpyridinium chloride catalyst is omitted.

pressured to 204 atm with carbon monoxide, and the mixture agitated at ambient temperature (30° C.).

After removing the excess gas from the reactor, 24.7 g of light yellow liquid product containing some suspended white solids was recovered.

Analysis of this liquid product fraction confirmed the presence of p-tolualdehyde; o-tolualdehyde was not detected.

This experiment confirms that toluene may be selectively carbonylated to p-tolualdehyde at ambient temperatures using an aluminum halide-alkylpyridinium catalyst system.

What is claimed is:

1. A process for the selective carbonylation of toluene to p-tolualdehyde which comprises mixing an N-alkylpyridinium halide and an anhydrous aluminum halide melt catalyst with toluene and carbon monoxide at an ambient temperature of about 0° C. to 200° C. and at a pressure of about 1 atm to about 300 atm until the desired tolualdehyde is formed, and separating the de-

TABLE I[a]

| | Melt Catalyst | TOLUENE CARBONYLATION TO p-TOLUALDEHYDE | | | | | | p-tolualdehyde |
|---|---|---|---|---|---|---|---|---|
| | | Operating Conditions | | | Product Composition | | | |
| Example | Composition | Temp.(°C.) | Pres.(atm) | Time(hrs) | p-CH$_3$C$_6$H$_4$CHO | O—CH$_3$C$_6$H$_4$CHO | C$_7$H$_8$ | Selectivity(%) |
| II | AlCl$_3$—BupyCl | 100 | 194 | 4 | 10.2 | 1.4 | 84.4 | 65 |
| III | AlCl$_3$—BupyCl | 130 | 197 | 4 | 7.2 | 1.1 | 86.6 | 54 |
| IV | AlCl$_3$—BupyCl | 160 | 194 | 4 | 8.4 | 1.3 | 85.0 | 56 |
| V | AlCl$_3$—PrpyCl | 100 | 194 | 4 | 7.8 | 1.0 | 87.0 | 60 |
| VI | AlCl$_3$ — | 100 | 197 | 4 | 5.0 | 0.8 | 78.7 | 23 |
| VII | — BupyCl | 100 | 204 | 4 | 0.2 | | 99.1 | 22 |

[a]Operating conditions as per Example I unless otherwise specified.

From the data in Example I and Table I which disclose the use of aluminum chloride-alkylphosphonium chloride melts as catalysts for the selective carbonylation of toluene to p-tolualdehyde it may be noted that:

(1) p-tolualdehyde is generated as the predominant product in with 71% selectivity in Example I using AlCl$_3$-BupyCl as catalyst and the described procedure. The ratio of p-tolualdehyde to o-tolualdehyde is ca. 7:1.

(2) Other experiments in Table I disclose the formation of p-tolualdehyde in up to 10% of the crude liquid product.

(3) Very little carbonylation is observed in the absence of aluminum chloride, using BupyCl only. In the absence of quaternary salt, aluminum chloride yields p-tolualdehyde as a minor product with 23% selectivity.

(4) Other catalyst compositions, such as AlCl$_3$-PrpyCl, are also effective under the screening conditions.

EXAMPLE VIII

A mixture of N-butylpyridinium chloride (8.58 g, 50 mmole), aluminum chloride (anhydrous, 6.67 g, 50 mmole) and toluene (10.0 g, 109 mmole) was transferred in a glass liner under argon purge to an 850 ml capacity pressure reactor, equipped with heating and means of agitation. The reactor was sealed, flushed with CO and sired product.

2. The process of claim 1, wherein the N-alkylpyridinium halide is N-butylpyridinium chloride.

3. The process of claim 1, wherein the aluminum halide is aluminum trichloride.

4. The process of claim 1, further comprising the use of only one equivalent of catalyst.

5. A process for syntheses of p-tolualdehyde which comprises subjecting a mixture of toluene and carbon monoxide to the action of an aluminum chloride-N-butylpyridinium chloride 'melt' catalyst at a temperature of about 0° C. to 200° C. and a pressure of 1 atm to 300 atm, wherein the ratio of toluene to catalyst mixture is from 0.1 to 10 and thereafter separating the p-tolualdehyde produced from said mixture.

6. A process for the synthesis of p-tolualdehyde which comprises subjecting a mixture of toluene and carbon monoxide to the action of an aluminum chloride-N-butylpyridinium chloride melt catalyst at a pressure of about 1 atm to 300 atm, wherein the improvement comprises use of ambient temperatures of about 0° C. to 200° C. and use of only one stoichiometric equivalent of aluminum chloride-N-butylpyridinium chloride catalyst rather than excess, and thereafter separating said p-tolualdehyde thus produced from said mixture.

* * * * *